United States Patent
Thompson

[11] Patent Number: 5,929,342
[45] Date of Patent: Jul. 27, 1999

[54] METHOD FOR MONITORING THREE PHRASE FLUID FLOW IN TUBULARS

[75] Inventor: Laird Berry Thompson, Dallas, Tex.

[73] Assignee: Mobil Oil Corporation, Fairfax, Va.

[21] Appl. No.: 08/858,239

[22] Filed: May 19, 1997

Related U.S. Application Data

[63] Continuation-in-part of application No. 08/633,269, Apr. 16, 1996, abandoned.

[51] Int. Cl.[6] ........................................................ G01F 1/74
[52] U.S. Cl. ............................................................ 73/861.04
[58] Field of Search ........................... 73/861.04, 861.28, 73/861.27, 861.18

[56] References Cited

U.S. PATENT DOCUMENTS

| | | | |
|---|---|---|---|
| 4,197,753 | 4/1980 | Harting et al. | 73/766 |
| 4,354,219 | 10/1982 | Akita | 73/861.08 |
| 4,751,842 | 6/1988 | Ekrann et al. | 73/61.1 |
| 5,001,936 | 3/1991 | Baumoel | 73/861.18 |
| 5,035,147 | 7/1991 | Woodward | 73/861.28 |
| 5,226,319 | 7/1993 | Sizuki | 73/204.14 |
| 5,228,347 | 7/1993 | Lowell et al. | 73/861.28 |
| 5,551,287 | 9/1996 | Maute et al. | 73/152.02 |

Primary Examiner—George M. Dombroske
Assistant Examiner—Jewel Thompson
Attorney, Agent, or Firm—Malcolm D. Keen

[57] ABSTRACT

Multi-phase fluid flow in a pipeline or other flowline is monitored using a combination of flow type detectors. One set of detectors monitors the interfaces between fluid interfaces and the other monitors the presence of different fluid phases around the periphery of the flowline. The relative volumetric fluid flow rates can be measured by detecting changes in the phase interfaces between two sets of sensor rings using sensors spaced around the flowline with the fluid flow type being detected across the flowline with an annular capacitance detector. The sensor rings typically use ultrasonic transducers for detecting the phase interfaces while the capacitance device indicates the presence (or absence) of different phases around the periphery of the flowline. By combining the outputs of the different detectors, an indication of the flow phenomena in the flowline can be obtained. The flowrate in the line can be measured directly using a concentrically oriented set of hot wire anemometers or a concentrically oriented set of thermopiles spaced equally around the flowline in conjunction with the annular capacitance device.

9 Claims, 2 Drawing Sheets

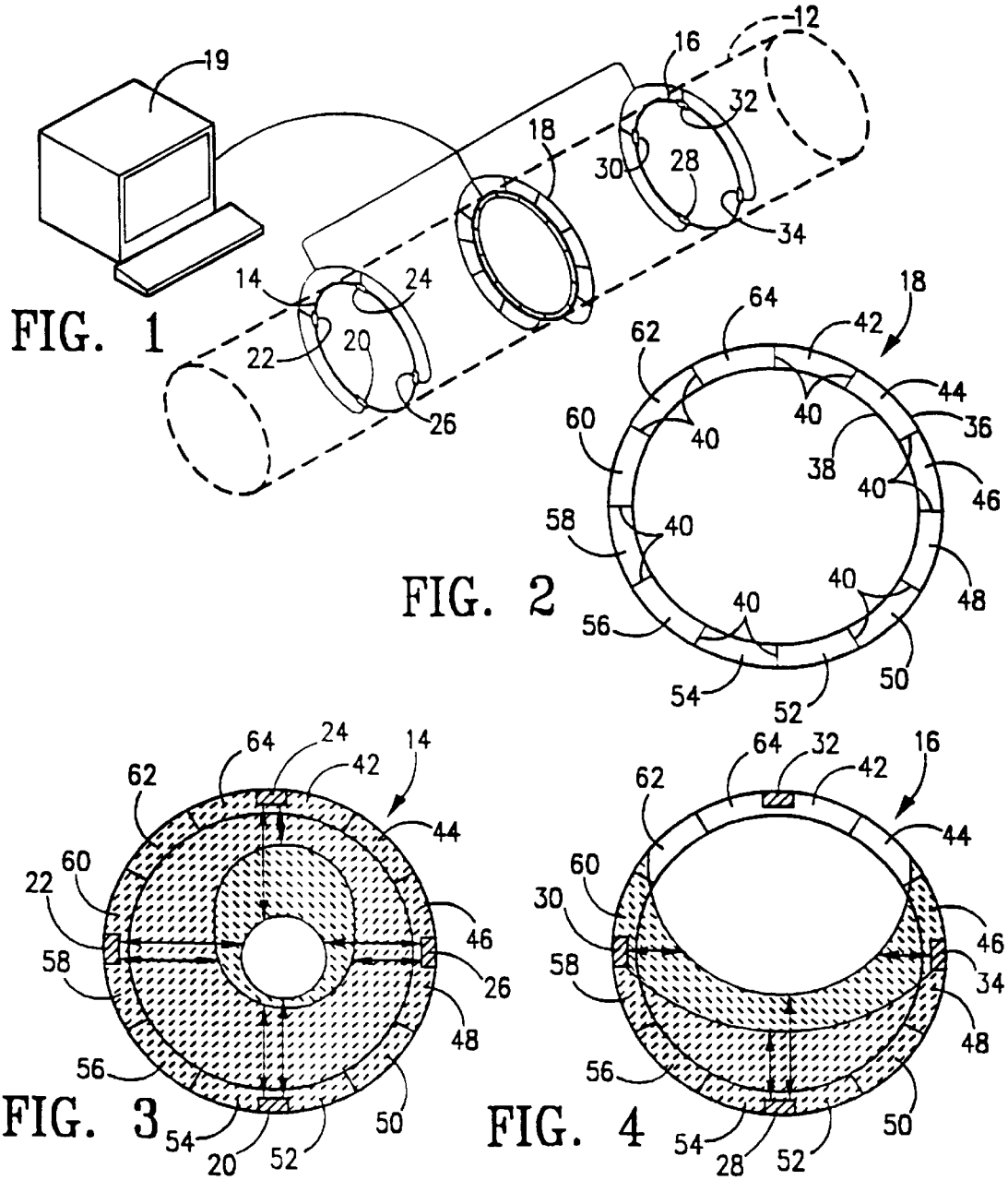

METHOD FOR MONITORING THREE PHRASE FLUID FLOW IN TUBULARS

CROSS REFERENCE TO RELATED APPLICATIONS

This application is a continuation in part of application Ser. No. 08/633,269, filed Apr. 16, 1996, now abandoned.

FIELD OF THE INVENTION

The present invention relates to measuring the volumes and flow rates and more particularly to measuring volumes and flow rates of multiphase fluids containing liquid hydrocarbon, water and gas in well heads and pipelines.

BACKGROUND OF THE INVENTION

In current practice, measurements of single phase flow are made using ultrasonics, such as Doppler shift in liquids which carry suspended solid particles, and various types of spinners, such as gas flow gauges. Two phase liquid flow can also be measured by using ultrasonics, such as Controllotron™ ultrasonic gauges, to precisely locate the liquid to liquid interface. Intrusive capacitance gauges are also used to identify the composition of a liquid in a pipe. Finally, in prior art, ultrasonics are used to recognize slug flow, such as, a liquid slug in a gas flow or a gas slug in a liquid flow.

U.S. Pat. No. 4,215,567 (Vicek) describes a method and apparatus for testing a production stream comprised of oil, water, and gas flowing through a conduit to determine the percentages of oil, water, and gas in the stream. A sample portion of the production stream is pumped through a sample line into a sample chamber where it is heated and allowed to remain for a retention period to substantially separate the sample portion into oil and water layers. Gas that evolves from the sample portion is vented from the chamber. At the end of the retention period, the sample portion is pumped back through the sample line into the conduit. As the sample portion flows through the same line the oil and water content of the sample and the volume of the sample are measured to determine the oil and water percentages in the sample portion. Also, the volume of the sample portion is measured as it is pumped through the sample line into the sample chamber and by comparing this volume with the volume of the sample portion pumped back into the conduit, the gas-liquid ratio of the sample portion can be determined.

U.S. Pat. No. 3,246,145 (Higgins) describes a system for determining the relative density of a liquid. The system includes a test chamber into which the liquid is introduced for testing purposes. A radioactive source is positioned on one side of the chamber for directing radiation through the chamber by way of the liquid in the chamber, and a radiation detector is positioned on the other side of the chamber for detecting radiation passing through the liquid and the chamber. At least a portion of the walls of the chamber between the source and the detector are of material relatively transparent to low energy radiation. With such structure, the low energy radiation will be allowed to pass freely from the source into the liquid and from the liquid to the detector. An energy discriminator responsive to only a predetermined low energy range is interconnected with the detector, and interconnected with the discriminator is a recorder for recording an indication of the radiation detected within the low energy range.

The problem not answered in prior art is to measure a three phase flow such as the combination of oil, water and gas in a single flowline. To date there is no monitoring device which can perform this function. It is therefore an object of the present invention to provide an apparatus for measuring three phase flow and also for determining the flow regime in the pipe whether it is slug flow, stratified flow or annular flow.

SUMMARY OF THE INVENTION

The present invention relates to measuring three phase flow of fluids, i.e. liquid hydrocarbon, water and gas in a single flowline, through a pipe. These devices may be installed at or near well heads in a producing oil and gas condensate field to monitor the contribution of each phase from each well over time. The combined flow of the well heads may be directed to a large diameter gathering line and conducted to an offshore platform or onshore surface facility with a separator. Total flow from the grouping of wells may be monitored at the separator, and ratios of each fluid calculated for each well. In this fashion, daily monitoring of each well is done and changes in fluid types are noted. A problem well, one in which an increase in unwanted fluids such as water or gas occurs, could be easily identified and remedial action on that well could taken. The present invention uses the flow measuring technologies of ultrasonic sound and electrical capacitance.

According to the present invention, the apparatus for measuring multi-phase fluid flow in a flowline comprises a ring of sensor detectors spaced equally around the flowline for detecting phase interfaces within the flowline; and an annular capacitance detector for determining fluid flow type along and across the flowline.

The preferred embodiment of the present invention consists of two rings of ultrasonic sensors and one ring of capacitance plates. The ultrasonic rings may be comprised of four transducers each located at the top of the pipe, the bottom of the pipe and at the midpoint of the pipe sides fully orthogonal to the top and bottom transducers. The positioning of each transducer and the location of the two rings provides the desired information about the location and motion of gas-liquid and liquid-liquid interfaces within the pipe.

The capacitance ring may have a pair of capacitance plates oriented concentrically within the pipe very close to the pipe wall. The pipe wall itself may be used as a capacitance plate if the proper material were used. The capacitance ring may be electrically isolated into approximately twelve arcs around the circumference of the pipe. Each arc registers the dielectric constant of the fluid flowing over that portion of the annulus and is used to determine the composition of the fluid, whether water, liquid hydrocarbon or gas. The capacitor plates are also open to influxing fluid. This allows measurement of the dielectric constant of the influxing fluid to distinguish water from hydrocarbon, and possibly oil from gas across the flowline. The measurement of capacitance is indicated by a capacitance indicator. Taken together with the output from the ultrasonic sensors, the capacitance measurement indicates the type of fluid flow occurring in the flowline and the relative volumetrics of the fluid flows.

By mapping the internal volumetrics of the three phases using the present invention, the relative proportions of each fluid at each well-head may be measured. The ratios of these fluids to the total production volumes monitored at the field separator is used to monitor well-head production of each phase over time.

THE DRAWINGS

FIG. 1 illustrates a section of pipe with two rings of ultrasonic transducers and a capacitance ring between the two rings of ultrasonic transducers.

FIG. 2 illustrates a detail of the capacitance ring of FIG. 1.

FIG. 3 illustrates a cross-section of the pipe with four ultrasonic transducers and the capacitance ring with gas in the center of the pipe surrounded by liquid hydrocarbon and water.

FIG. 4 illustrates stratified flow with water on the low side of the pipe overlain by liquid hydrocarbon and gas.

DETAILED DESCRIPTION

Figure 5:
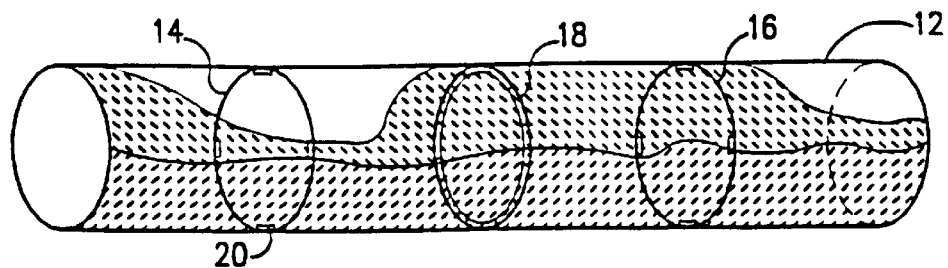
FIG. 5 illustrates the pipe as depicted in FIG. 1 with water, liquid hydrocarbon and gas slugs predicting the appearance of slug flow regime in the pipe.

Referring to FIG. 1, the multiphase monitoring tool is illustrated on pipe section 12 with three measurement sensor rings 14, 16 and 18. Measurement sensor rings 14, 16 and 18 are preferably mounted within pipe section 12 prior to installation in a pipeline. In the alternative, each sensor ring may be mounted within a portion of pipe section 12 to be joined together at a later time. The pipe is shown in a horizontal position but the tool will function with the pipe in other angular positions, e.g. at angles intermediate horizontal and the vertical.

Measurement sensor ring 14 consists of ultrasonic transducers 20, 22, 24 and 26 and measurement sensor ring 16 consists of ultrasonic transducers 28, 30, 32 and 34, each set mounted orthogonal to each other at the top, sides and bottom of pipe section 12. These sensors are illustrated in more detail in FIGS. 3 and 4. These sensor rings may consist of more sensors, such as the ultrasonic sensor rings may consist of 8 to 16 sensors equally spaced around the internal circumference of the pipe beginning at the top. The positioning of each transducer and the location of the two rings provides the desired information about the location and changes between the gas/liquid/liquid interfaces within the pipe at the locations of the rings.

The third measurement sensor ring 18 is a concentric set of capacitance plates 36 and 38 shown in the middle of pipe section 12 in FIGS. 1 and 2. An enlargement of measurement sensor ring 18 is shown in FIG. 2. The concentric arrangement of capacitance plates 36 and 38 has several non-conducting dividers 40 resulting in the creation of several individual capacitance arcs 42–64 within the ring. There are twelve arcs in the present invention, however, other embodiments of the present invention might contain more or fewer arcs. For example, the concentrically oriented set of capacitance plates used for the purpose of measuring the areal extent of each fluid phase in the annulus of the pipe can be divided into 8 to 24 arcs of discrete capacitance depending on sensitivity needed. Each arc registers the capacitance and hence the dielectric constant of the fluid flowing over that portion of the annulus and in so doing provides an indication of the composition of the fluid flow at that point—water, liquid hydrocarbon or gas.

In FIG. 1 wiring coming from each measurement sensor in both ultrasonic measurement sensor ring 14 and 16 and capacitance measurement sensor ring 18 are illustrated as connecting to computer 19 which is located a central facility (not shown) to monitor the measurement sensor installations. The sensor data obtained by measurement sensor rings 14, 16 and 18 will provide an accurate measurement of the cross-sectional area of pipe section 12 for each fluid phase. By measuring the elapsed time for a specific phase interface differential to move between the two spaced apart ultrasonic sensor rings, it is possible to derive a measurement of the flow rate in the pipe. A series of phase measurements derived from the cross-sections could then be summed to arrive at the relative volume flows for each phase. By measuring the combined flow of all wells at an installation (probably at a separator in a centralized facility), it is possible to measure the relative contribution of each well-head for each fluid type.

A number of different flow regimes may be encountered at producing well-heads. FIG. 3 shows the measurement theory applied to recognizing and monitoring annular flow. Annular flow typically occurs when gas rates and overall production rates are high. The gas moves within the center of the pipe and liquids move through the annulus between the gas bubble and the pipe wall.

In annular flow, the capacitance plates around the inside wall of the pipe should indicate water through all 360 degrees in the situation illustrated in FIG. 3. In the figures, gas is illustrated as white, liquid hydrocarbon is illustrated as having lines slanted to the left, (from bottom to top) and water is illustrated as having lines slanted to the right (from bottom to top). The gas/liquid interface can be detected by the ultrasonic signal from the transducers. A very strong reflection will occur at the interface, and the travel time from the transducer to that interface and back will be easily measured. More difficult is the liquid/liquid interface of the oil and water which positioned between the gas the transducer. This interface is found using ultrasonics in two-phase liquid flow technology. With the present invention, it is then possible to identify the relative area occupied by all three fluids in the pipe.

By monitoring the changing ratios of the areas and by having a total volume rate measured at a collecting location, it is then possible to back out the relative rates of flow for the three phases and their change through time.

FIG. 4 shows an example of stratified flow. This flow regime can be detected and measured using both the capacitance ring and the ultrasonics sensors. The capacitance permits determination of what area of the pipe wall or other flowline wall is occupied by gas, water and liquid hydrocarbon. The ultrasonic sensor also perform a diagnostic function. Top transducer 32 will not be able to propagate a sonic wave through the gas. Side transducers 30 and 34 will also probably receive no return signal unless the gas/liquid interface happens to occur perpendicular to each transducer. Bottom transducer 28, however, should get a clear sign of the gas/liquid interface. The transmitted and received signal from transducer 28, plus the capacitance data should allow for areal computation.

Alternative embodiments of the present invention might have more ultrasonic transducers in measurement sensor ring 14 in order better image the gas/liquid interface. For example, six, eight or even ten transducers might be needed to accurately image the stratified fluid flow illustrated.

FIG. 5 illustrates a slug flow regime in pipe 12. Again capacitance ring 18 provides information as to the location of the liquid/liquid interface and the ultrasonic measurement sensor rings 14 and 16 detect the gas slugs moving along the pipe. Knowing the precise distance between measurement sensor rings 14 and 16 allows further volumetric computations for the gas portion of flow.

Other embodiments of the present invention may be designed to measure flow rates of the fluids directly, particularly near the outside rim of the annulus. For example, a second capacitance ring near the first may indicate rapid small scale changes in the liquids which indicate their speed.

For example, a wavy liquid-to-liquid or gas-to-liquid interface may move along the annulus, and its velocity may be measured as just described by the two spaced apart sensors. Another embodiment may be to install a sparker just upstream of the first measurement sensor ring 14 with its transducers. Short bursts of bubbles could be generated and their travel time moving with the liquid between measurement sensor rings 14 and 16 calculated. Thus, the liquid velocities could be measured. In other words, where a sparker is placed in the bottom of the pipe just upstream of the first sensor ring to produce a series of bubbles in the fluid flow, the bubble stream can be monitored as it passes the rings and the flow rate calculated.

Figure 6:
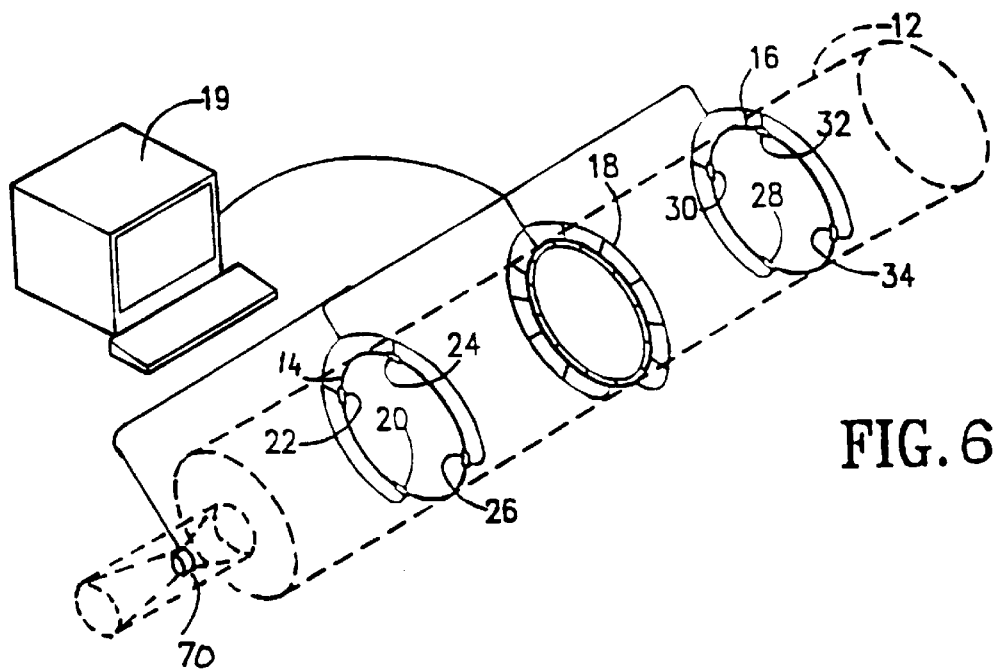
FIG. 6 illustrates the use of a gas flow venturi meter in combination with the other sensors.

The gas flow rate in the pipe may be directly and independently measured by the use of a venturi meter as shown in FIG. 6. A venturi meter 70 of conventional type is positioned upstream or downstream of the pipe section with the sensors to obtain an indication of the gas flow rate which can be combined with the flow rate measurements from the ultrasonic and capacitance sensors to obtain an indication of the relative flow rates. The output from venturi meter 70 is taken to computer 19 where it is combined with the outputs from the other sensors which can then be used to derive the information about the liquid interfaces and flows in the pipe.

Rings of temperature sensors and hot-wire anemometers could also be used for directly measuring flow rates by monitoring the in situ temperatures and the amount of cooling on successive hot wires. This disposition of these sensors would be similar to the capacitance ring and work in combination with it. This ring of sensors may include a concentrically oriented set of hot wires anemometers or thermopiles for measuring the flow rate of each fluid phase in the annulus of the pipe. This thermo-sensitive ring will be divided into 8 to 24 arcs of discrete capacitance depending on sensitivity needed. This embodiment may also include set temperature sensitive probes which monitor the temperature of the fluids in the annulus of the pipe. This temperature measurement, combined with the rate of temperature loss indicated by claim 10 will give flow rates for the fluids.

I claim:

1. Apparatus for measuring multi-phase flow in a flowline comprising:

at least two sensor ring means being positioned on said flowline and spaced from each other, each of said two sensor ring means having sensors spaced equally around the flowline for detecting changes in the phase interfaces within the flowline as the multi-phase flow passes therethrough, and at least one annular capacitance detector spaced from each of said at least two sensor ring means for determining fluid flow type across the flowline.

2. Apparatus according to claim 1 in which the sensor rings comprise ultrasonic transducers.

3. Apparatus according to claim 1 in which the annular capacitance detector includes a concentrically oriented set of capacitance plates for the purpose of measuring the areal extent of each fluid phase in the flowline.

4. Apparatus according to claim 3 in which the capacitance plates are divided into a predetermined number of arcs of discrete capacitance.

5. Apparatus according to claim 1 also means, for measuring gas flow rate and for correlating the measured gas flow rate with the fluid flow rates determined by the sensors.

6. Apparatus according to claim 1 including a concentrically oriented set of hot wire anemometers or a concentrically oriented set of thermopiles for measuing flow rate in the flowline.

7. A method for measuring multi-phase fluid flow in a flowline comprising the steps of:

determining phase interfaces in the multi-phase fluid flow at a first location with a sensor ring having sensors spaced around the flowline, determining the phase interfaces in the multi-phase fluid flow at a second location, downstream of the first location with a sensor ring having sensors spaced around the flowline, detecting changes in the phase interfaces from the first location to the second location; and determining fluid flow type across the flowline using an annular capacitance detector.

8. The method according to claim 7 in which the fluid flow type across the flowline is determined by measuring the areal extent of each fluid phase in the flowline with a concentrically oriented set of capacitance plates.

9. The method according to any of claims 6 to 8 which includes the step of measuring the gas flow rate with means for measuring gas flow rate and correlating the measured gas flow rate with the fluid flow measurements of the sensors.

* * * * *